(12) United States Patent
Arefieg (10) Patent No.: US 10,318,915 B2
(45) Date of Patent: Jun. 11, 2019

(54) HEALTHCARE SYSTEM FOR RECORDING AND MONITORING TRANSACTIONS OF SYSTEM PARTICIPANTS

(71) Applicant: Thuban, Inc., Ridgefield, CT (US)

(72) Inventor: Rana J. Arefieg, Ridgefield, CT (US)

(73) Assignee: Thuban, Inc., Ridgefield, CT (US)

( * ) Notice: Subject to any disclaimer, the term of this patent is extended or adjusted under 35 U.S.C. 154(b) by 983 days.

(21) Appl. No.: 14/037,104

(22) Filed: Sep. 25, 2013

(65) Prior Publication Data
US 2014/0088997 A1  Mar. 27, 2014

Related U.S. Application Data

(60) Provisional application No. 61/705,961, filed on Sep. 26, 2012.

(51) Int. Cl.
  *G06Q 10/08* (2012.01)
  *G06Q 50/22* (2018.01)
  *G16H 40/20* (2018.01)

(52) U.S. Cl.
  CPC .......... *G06Q 10/087* (2013.01); *G06Q 50/22* (2013.01); *G16H 40/20* (2018.01)

(58) Field of Classification Search
  CPC ...... G06Q 50/22; G06Q 50/24; G06Q 10/087; G06Q 10/08; G06Q 10/0833;
  (Continued)

(56) References Cited

U.S. PATENT DOCUMENTS 4,226,235 A   10/1980   Sarnoff et al.
4,329,988 A    5/1982   Sarnoff et al.
(Continued)

FOREIGN PATENT DOCUMENTS

EP   1102194   5/2001
EP   1281351   2/2003

OTHER PUBLICATIONS

"Is the government watching you?, The FDA clarifies sample signature procedures", PharmExec.com, Jan. 1, 2003.*
(Continued)

*Primary Examiner* — Joseph D Burgess
(74) *Attorney, Agent, or Firm* — David M. Quinlan, P.C.

(57) ABSTRACT

A centrally controlled healthcare environment interconnects manufacturers of medical products, healthcare providers, and patients in a manner that provides a variety of functionalities. A particularly advantageous application of the system provides a mechanism for regulating and recording the flow of free drug samples from manufacturers to healthcare providers and then to patients. This involves a method by which a unique record is created each time it changes hands on the way from the manufacturer to the patient. A machine-readable unique code assigned to the sample is scanned automatically when the sample it is withdrawn from inventory at the manufacturer. The code and a unique identity of the individual withdrawing the sample are stored as a first record. This process is repeated at each location and for each individual handling the sample, including when it reaches the healthcare provider. Thus, a series of unique records is created that track the sample.

15 Claims, 3 Drawing Sheets

(58) Field of Classification Search
CPC .............. G06Q 30/0609; G06F 19/322; G06F 19/3456; G06F 19/3462
See application file for complete search history.

(56) References Cited

U.S. PATENT DOCUMENTS

| | | | |
|---|---|---|---|
| 4,578,064 A | 3/1986 | Sarnoff et al. | |
| 4,731,726 A | 3/1988 | Allen | |
| 5,019,974 A | 5/1991 | Beckers | |
| 5,536,249 A | 7/1996 | Castellano | |
| 5,593,390 A | 1/1997 | Castellano | |
| 5,728,074 A | 3/1998 | Castellano | |
| 5,822,715 A | 10/1998 | Worthington | |
| 5,840,020 A | 11/1998 | Heinonen | |
| 5,925,021 A | 7/1999 | Castellano et al. | |
| 6,021,392 A | 2/2000 | Lester et al. | |
| 6,175,752 B1 | 1/2001 | Say et al. | |
| 6,192,891 B1 | 2/2001 | Gravel et al. | |
| 6,302,855 B1 | 10/2001 | Lav et al. | |
| 6,544,212 B2 | 4/2003 | Galley et al. | |
| 6,875,195 B2 | 4/2005 | Choi | |
| 6,906,802 B2 | 6/2005 | Voelkel | |
| 6,996,538 B2 | 2/2006 | Lucas | |
| 7,427,275 B2 | 1/2008 | DeRuntz et al. | |
| 7,404,796 B2 | 7/2008 | Ginsberg | |
| 7,534,230 B2 | 5/2009 | Follman et al. | |
| 7,591,801 B2 | 9/2009 | Brauker et al. | |
| 7,737,858 B2 | 6/2010 | Matityaho | |
| 7,871,393 B2 | 1/2011 | Monroe | |
| 7,988,630 B1 | 8/2011 | Osorio et al. | |
| 8,044,778 B2 | 10/2011 | Monroe | |
| 8,149,111 B2 | 4/2012 | Monroe | |
| 8,206,340 B2 | 6/2012 | Arefieg | |
| 8,260,340 B2 | 6/2012 | Arefieg | |
| 8,361,026 B2 | 1/2013 | Edwards et al. | |
| 8,366,682 B2 | 2/2013 | Wyrick | |
| 9,357,961 B2 | 6/2016 | Arefieg | |
| 9,358,334 B2 | 6/2016 | Arefieg | |
| 2002/0013522 A1 | 1/2002 | Lav et al. | |
| 2002/0016719 A1 | 2/2002 | Nemeth et al. | |
| 2003/0028089 A1 | 2/2003 | Galley et al. | |
| 2003/0127508 A1* | 7/2003 | Jones ................ G06Q 10/087 235/375 |
| 2005/0075954 A1 | 4/2005 | Matsumoto et al. | |
| 2006/0135874 A1 | 6/2006 | Peng | |
| 2006/0173406 A1 | 8/2006 | Hayes et al. | |
| 2006/0224417 A1* | 10/2006 | Werner ................ G06F 19/366 705/2 |
| 2007/0055586 A1 | 3/2007 | Lucas | |
| 2007/0066938 A1 | 3/2007 | Iio et al. | |
| 2007/0186923 A1* | 8/2007 | Poutiatine ............. A61J 7/0038 128/200.14 |
| 2007/0197968 A1 | 8/2007 | Pongpairochana et al. |
| 2008/0119705 A1 | 5/2008 | Patel et al. |
| 2008/0269673 A1 | 10/2008 | Butoi et al. |
| 2008/0306434 A1 | 12/2008 | Dobbles et al. |
| 2009/0105570 A1 | 4/2009 | Sloan et al. |
| 2009/0137957 A1 | 5/2009 | Wagener |
| 2009/0138207 A1 | 5/2009 | Cosentino et al. |
| 2009/0194587 A1* | 8/2009 | DeVet .................... G06Q 10/08 235/385 |
| 2010/0010330 A1 | 1/2010 | Rankers et al. |
| 2010/0016700 A1 | 1/2010 | Sieh et al. |
| 2010/0090004 A1 | 4/2010 | Sands et al. |
| 2010/0141457 A1 | 6/2010 | Wass et al. |
| 2010/0256593 A1 | 10/2010 | Yodfat et al. |
| 2011/0082711 A1 | 4/2011 | Poeze et al. |
| 2011/0184264 A1 | 7/2011 | Galasso et al. |
| 2011/0282173 A1 | 11/2011 | Fonduca et al. |
| 2011/0320130 A1 | 12/2011 | Valdes et al. |
| 2012/0046606 A1 | 2/2012 | Arefieg |
| 2012/0047049 A1 | 2/2012 | Cadiz |
| 2012/0130534 A1* | 5/2012 | Wurm ................. G07F 17/0092 700/236 |
| 2012/0173287 A1* | 7/2012 | Cowand ............... G06Q 10/087 705/3 |
| 2012/0203566 A1 | 8/2012 | Kidd et al. |
| 2012/0238853 A1 | 9/2012 | Arefieg |
| 2012/0278228 A1 | 11/2012 | Rubinstein |
| 2014/0048593 A1* | 2/2014 | Hoganson ........ G06Q 10/06316 235/376 |
| 2014/0142507 A1 | 5/2014 | Armes |

OTHER PUBLICATIONS

International Search Report and Written Opinion, dated Mar. 20, 2015, in PCT Appln. No. PCTUS14/16648.
EPO Search Report dated Oct. 10, 2016, in EP Appln. No. 11818470.4.
Humapen Memoir Insulin Delivery Device User Manual, Eli Lilly & Company, 2006.
"A New Era in Blood Glucose Monitoring Begins: The Accu-Chek Mobile System," Trade News, Vienna, Austria, Roche Diabetes Care, Sep. 30, 2009.
Walsh, J., "Concept 2: The Smart Insulin Pen," www.diabetesnet.com/diabetes_technology/smart_pen.php (last visited Mar. 25, 2010).
International Search Report and Written Opinion, dated Oct. 31, 2011 in PCT Appln. No. PCT/US11/01349.
Thomas, Katie, "Tiny Lifesaver for a Growing Worry," New York Times, Sep. 8, 2012, pp. B1-B2.
FedEx Express, https://en.wikipedia.org/wiki/FedEx_Express, last visitied Jul. 27, 2018.

* cited by examiner

HEALTHCARE SYSTEM FOR RECORDING AND MONITORING TRANSACTIONS OF SYSTEM PARTICIPANTS

CROSS REFERENCE TO RELATED APPLICATIONS

The present application claims benefit of provisional application No. 61/705,961, filed Sep. 26, 2012, the contents of which are incorporated herein as if set out in full.

BACKGROUND OF THE INVENTION

Field of the Invention

The present invention relates to a healthcare system, and more particularly, to a healthcare system that enables communication among suppliers, providers, patients, and regulatory agencies to provide comprehensive management of numerous aspects of transactions among the system participants.

Description of Related Art

One focus of automated healthcare management systems has been centralized inventory control. U.S. Pat. No. 6,996,538 in some ways exemplifies the many such systems disclosed in the prior art. This patent describes a system for controlling healthcare supply inventories that keeps track of usage of healthcare supplies, enables automatic ordering for replacing inventory as it is used, and automates billing. Such an inventory control system is particularly useful for large medical practices and hospitals. However, this system and systems like it, such as those described in U.S. Pat. Nos. 6,021,392, 7,737,858, Pub. No. US 2005/0075954, Pub. No. US 2010/0090004, and Pub. No. US 2010/0141457, do not enable the various participants in the system, especially physicians, to monitor transactions in a manner that can prevent fraud and other abusive behaviors practiced by some segments of the healthcare industry which can jeopardize patient well-being. Some prior inventory control systems also include additional functionalities, such as sharing data on usage of products with government bodies or public health institutions and interfacing with insurance providers. Examples of inventory control systems with these kinds of added functionalities can be found in Pub. No. US 2012/0047049, Pub. No. US 2012/0203566, and Pub. No. US 2012/0278288. However, these systems are also not directed toward preventing behaviors that can jeopardize patient care.

Pub. No. US 2012/0173287 discloses an Internet-based inventory control system in which pharmaceutical manufacturers, healthcare providers such as physicians and pharmacies, and patients can all participate. It also discloses a "sample closet" maintained by healthcare providers for managing free medication samples provided by pharmaceutical manufacturers. As those familiar with today's healthcare landscape know, such samples are an important aspect of most healthcare providers' patient care activities. Pub. No. US 2012/0173287 discusses some of the ways such samples benefit healthcare providers, but it does not discuss ways to maintain strict control over the receipt and dispensing of such samples to prevent adverse effects on patient care. The present invention addresses those shortcomings, as will be discussed in detail in the discussion below of preferred embodiments of the present invention and methods for implementing them.

Another aspect of the present invention advantageously incorporates the patient treatment device disclosed in U.S. Pat. No. 8,206,340 in the name of the present inventor. This device has multiple functionalities that facilitate patient self management of medical conditions such as diabetes. U.S. Pat. No. 9,357,961, also in the name of the present inventor, expands the functionality of the original device by describing embodiments that enable patient self-testing and -treatment of numerous specific pathologies as well as describing the enhanced functionality provided by enabling these types of devices to communicate with various components of a modern healthcare system. While the devices disclosed in the '340 and '961 patents have the ability to improve patient outcomes in and of themselves, their utility can be greatly enhanced beyond the intrinsic value of efficacious patient treatment by properly integrating them into an interconnected healthcare infrastructure such as that comprising an important part of the present invention.

Missing from the known prior art is an integrated healthcare system that is sufficiently "global" in scope to incorporate and provide intercommunication and interfunctionality among myriad aspects of a modern healthcare landscape, while maintaining a focus that protects the interests of healthcare providers and their patients.

SUMMARY OF THE INVENTION

It is an object of the present invention to provide a centrally controlled global healthcare system that enables healthcare providers to maximize the opportunities for positive outcomes in patient care.

It is another object of the present invention to integrate individual patient treatment devices into such a system in a manner that protects patients and healthcare providers from the consequences of improper practices.

A more specific object of the invention is to provide detailed tracking of drug samples that includes a record of each person handling the sample, from the manufacturer to the patient, in order to provide records that can be compiled and accessed by physicians, regulatory agencies, and patients.

This Summary is provided to introduce a selection of concepts in a simplified form that are further described below in the Detailed Description. This Summary is not intended necessarily to identify key or essential features of the claimed subject matter, nor is it intended to be used in determining the scope of the claimed subject matter

BRIEF DESCRIPTION OF THE DRAWINGS

The objects of the invention will be better understood from the detailed description of its preferred embodiments which follows below, when taken in conjunction with the accompanying drawings, in which like numerals and letters refer to like features throughout. The following is a brief identification of the drawing figures used in the accompanying detailed description.

Those skilled in the art will readily understand that the drawings are schematic and not strictly to scale, but nevertheless will find them sufficient, when taken with the detailed descriptions of preferred embodiments that follow, to make and use the present invention.

DETAILED DESCRIPTION OF PREFERRED EMBODIMENTS

Figure 1:
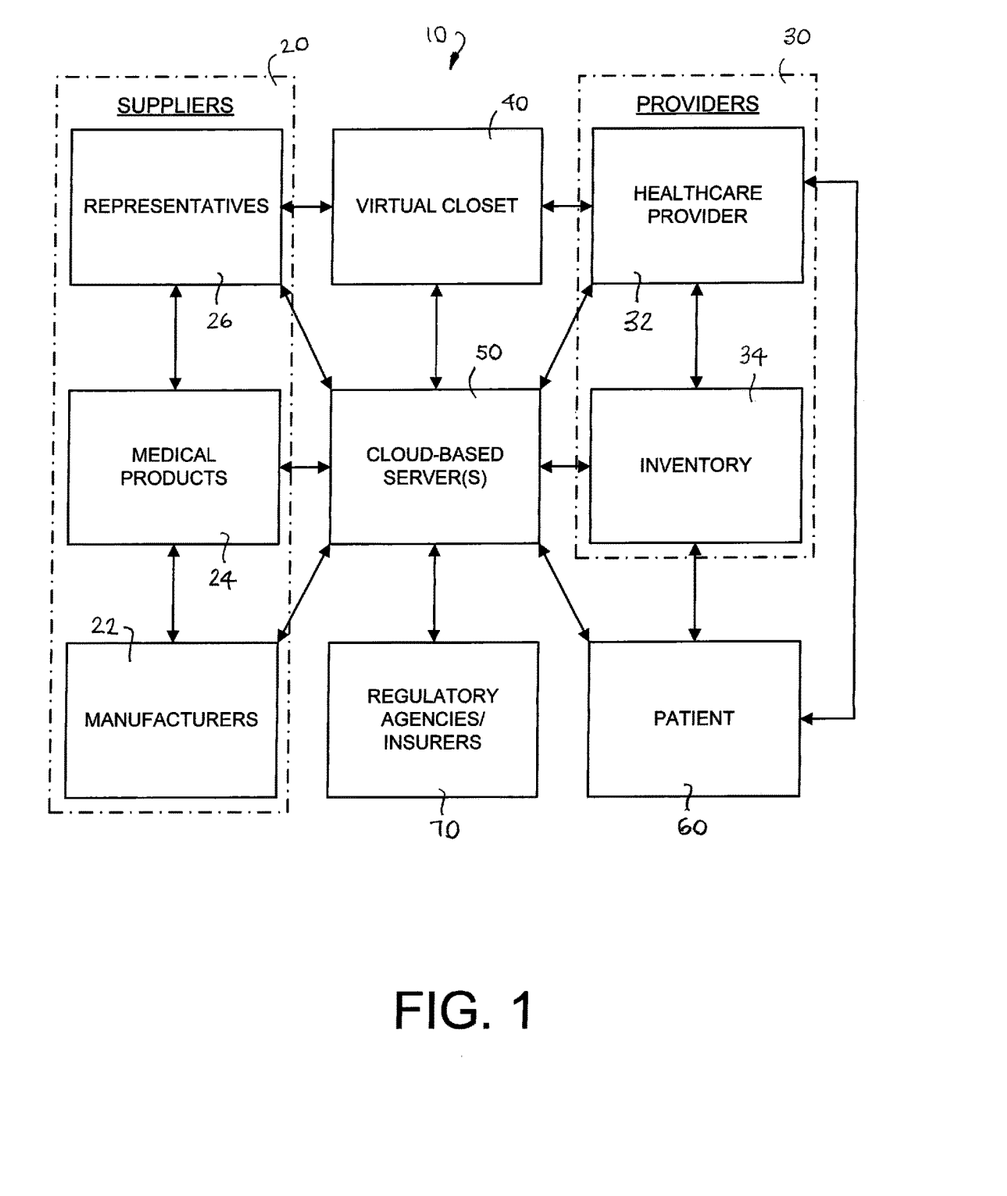
FIG. 1 is a schematic diagram of the architecture of a centrally controlled healthcare environment in accordance with one embodiment of the invention.

FIG. 1 is a schematic diagram used in conjunction with the description that follows to describe the architecture interconnecting various components of a comprehensive healthcare environment 10 in accordance with an embodiment of the present invention. The system embodying the environment 10 is centrally controlled in its salient aspects, and in a preferred application the participants subscribe to the system to use as many of the system functionalities as desired by the participant or permitted by the system administrator.

One component of a typical healthcare environment is multiple suppliers 20 of consumable items used in treating patients. Grouped into the category of suppliers for purposes of the present description are manufacturers 22 of any type of consumable medical product 24 that can be used by a healthcare provider to support its mission of providing health care to patients. In that sense, the terms "manufacturer" and "product" are used in a comprehensive sense to mean producers of specialized medical products used in a medical or dental practice, or by hospitals or clinics, such as pharmaceuticals, medical devices or prosthetics, educational and marketing materials, medication sample vouchers, practice management software, and the like. The terms also encompass producers of branded, generic, biosimilar, or over-the-counter medications or devices, wound-care products, consumer healthcare products, and other types of off-the-shelf items. The role of manufacturers 22 as part of the disclosed system, and the reasons for a separate conceptual depiction in FIG. 1 of the products they provide, will be better appreciated from the more detailed description further below of the interaction of the various component parts of the environment 10 in accordance with this embodiment.

Another relevant part of the supplier component of the environment 10 are representatives 26 of the manufacturers 22. In the healthcare industry today, personal representatives typically provide an important interface between healthcare providers and makers of special medical products, and perhaps to a lesser extent between healthcare providers and the manufacturers of off-the-shelf products. The healthcare environment 10 according to this embodiment of the invention accounts for the role that these personal representatives 26 play in delivering quality health care to the ultimate patient-consumer, which is why they are depicted in FIG. 1 as a separate functional component of the environment 10. The role of the representatives 26 in the context of the environment 10 and how they interact with the environment is an important aspect of the invention, as explained in more detail further below.

Providers 30 of healthcare to patients form another major component of a modern healthcare environment 10. In the depiction in FIG. 1 providers 30 include healthcare providers 32 that directly provide healthcare to patients and one or more repositories 34 of an inventory of items utilized by a healthcare provider 32 to administer care to patients or otherwise operate the healthcare facility. This description uses the term "healthcare provider" in a comprehensive sense to mean any entity that administers health care to patients. In that regard, a healthcare provider can be a doctor or a group of doctors comprising a medical practice, a dentist or group of dentists comprising a dental practice, a hospital, a nursing home or other elder care facility, a hospice, specialized or general practice clinics, and in the present embodiment, public emergency responders (911) and private emergency responders such as Alert One® medical alert service provided by Alert One Services, Inc., of Williamsport, Pa. In this description the collective stock of medical items (that is, one or more products 24) on hand at the healthcare provider facility and the physical repositories for such items in inventory are sometimes referred to interchangeably as "inventory." The usage in any given instance will be clear from the context.

The virtual closet 40 is an important part of the environment 10, and of an inventory/sample control system implemented as a part thereof. The virtual closet is a conceptual representation of a collective repository of information regarding the products 24 of the manufacturers 22 in the inventories 34 of the healthcare providers 30. The entire system is under the central control of one or more central servers 50. It is an important aspect of the system that all information flow and operational control involves the servers 50.

One example of how the central servers control the environment 10 is the operation of the virtual closet 40. Each of the inventory repositories 34 at a healthcare provider 30 will be provided with a way of keeping track of items (products 24) taken from inventory or placed therein to replenish supplies. Many of the prior art patents and publications mentioned at the outset describe details of effective systems for tracking medical supply inventories. The systems disclosed in U.S. Pat. No. 6,996,538 and Pub. No. US 2012/0173287, which are incorporated by reference herein, can readily be adapted by one skilled in this art for use with one or more inventory repositories 34 of a healthcare provider 32 in the context of the environment 10. By way of example, each inventory item (or at least selected items critical to the mission of the particular provider 30) can have a unique bar code, RFID tag, or other electronically readable identification device secured thereto that is detected by a reader at the repository 34 when the item is removed from the repository and/or placed therein. As discussed further below, it is an important aspect of the present embodiment that samples provided by manufacturers 22 and their representatives 26 are specifically accounted for in this fashion.

In addition, the person removing the item or stocking the inventory with the item will have either his or her own magnetically readable ID tag, or some other form of electronic identification to log into a computer terminal to indicate create a record of who made the item withdrawal or deposit. In addition, the person withdrawing the item will indicate the patient with whom the item will be used. If each patient at a healthcare facility has his or her own unique identifier stored in the facility's computer system, provider medical personnel assigned to a particular patient can be issued magnetic cards for the patient that can be presented for automatic reading when the item is withdrawn. An additional level of control and information can be provided if a record is made when the item is actually delivered or administered to the patient. Another example of a component of the inventory 34 is a pharmacy in a hospital or clinic from which a patient can directly receive items based on prescriptions from provider medical personnel. Various particulars of these transactions are also recorded and stored in a suitable fashion for purposes described further below.

Each healthcare provider 32 will store all of the transactions involving its inventory 34. It will be appreciated that a given provider 32 may have multiple locations at a given site where items are stocked and from which items can be withdrawn. A healthcare provider 32 may also comprise multiple facilities at different sites, each with its own separately controlled inventory locations throughout the facility. The architecture implementing the environment 10 provides maximum flexibility in how any given healthcare entity interacts with the system. One concept underlying the virtual closet 40 is to consider collectively the status of the inventories at different healthcare facilities, and optionally, even to consider separately individual inventories at the same healthcare provider if the provider subscribes to the system on that basis. The virtual closet concept also enables monitoring of the cumulative usage of medical items by multiple healthcare providers 26 and multiple healthcare product manufacturers 22. As will be apparent from the description further below of exemplary implementations of the system embodying the healthcare environment 10, the state and usage history of each healthcare provider's inventory, and the collective inventory state and usage history across the entire environment, enables more efficient inventory control by the healthcare providers 32 and better allocation of resources by the manufacturers 34.

The central server complex 50 enables the environment 10 to effect its myriad functions. The environment depicted schematically in FIG. 1 contemplates the use of multiple cloud-based servers accessed by the environment participants through the Internet. It will be readily apparent that other types of interconnections between one or more of the participants is within the scope of this disclosure. For example, some of the suppliers and healthcare providers might be part of a wide-area network connected by cable to the server complex, while other manufacturers and providers connect by computer links over the Internet. In any case, a preferred embodiment contemplates storage at the central server complex 50 of all transactions among the various participants. In FIG. 1 the virtual closet 40 is shown as a separate box, but it will be understood that this is a functional representation to facilitate understanding of how it operates in the context of the environment 10. In practice, the virtual closet 40 will typically be cloud-based and can be envisioned in one exemplary implementation as an operating module within the server complex 50.

In the context of inventory and sample control, as just discussed, salient facts regarding every withdrawal of an item from and placement (or replacement) of an item into inventory 34 at any healthcare provider 32 are stored at the central server complex. For inventory control, this can involve identification of the item itself and the location from which it was withdrawn, as well as any other information that is used by known inventory control systems such as those disclosed in the prior art already discussed. Manufacturers with access to the central server database can automatically restock items for which inventory at a particular provider location is running low by delivering the item to the inventory 34 at the provider location. This can be done in a variety of ways, such as by personal delivery, mail, via electronically delivered vouchers for samples, and the like. The central repository of usage data represented by the virtual closet also permits manufacturers to better understand relative demand among different items across the entire environment and allocate manufacturing resources accordingly. Manufacturers can also determine which healthcare providers are using more or less of their products and perhaps uncover quality control or consumer preference issues that can be addressed with an eye to increasing sales. By organizing usage data into broad categories, the system administrator in control of the system can provide manufacturers with information regarding which of its product categories are underperforming relative to its competitors' products in the same categories. For example, if a diabetes treatment product line of Manufacturer 1 is being used less than a diabetes product line of Manufacturer 2, Manufacture 1 might wish to undertake a survey of the locations where its products are underperforming. It is contemplated that members of the environment would agree to the collection and sharing of this kind of general marketing information since it would have the potential to benefit all participants equally. Other kinds of data, collected as products are used, have utility in other ways, as will be discussed as this description proceeds.

The environment 10 is also particularly adapted to provide heretofore unknown tracking and control of samples of medical supplies provided to healthcare providers or patients by manufacturers. As used herein, the term "sample" refers to any product provided by a manufacturer 22 to an end user for free or at a cost below the normal price charged to users of that type. The "value" of the sample to the user is the difference between the normal price and the price paid by the user. A "sample" within the meaning used herein is not limited in form, and can be, for example, a physical sample of a product (such as a container or seal-pack of tablets or other medication), a digital coupon redeemable by connecting to a website of the manufacturer, a paper or other form of voucher that can be presented to obtain a medical product, and the like. Vouchers provide value in a myriad of ways, such as being applicable to a supply of a medication covering a particular number of doses, a discount redeemable at a pharmacy, and contributions toward insurance co-pays, just to name a few examples. The unique manner in which samples are treated by a healthcare environment in accordance with the present embodiment of the invention is described in more detail further below.

Continuing with a description of the component parts of the environment 10 shown in FIG. 1, its framework also provides for incorporation of patients 60 as part of the environment 10. Patients can interact with other participants in the environment in a number of ways, as indicated by the arrows connecting patients 60 to healthcare providers 32, directly to the inventory 34 of a healthcare provider (for example, a pharmacy in a clinic or hospital, or even a stand-alone subscribing pharmacy), and to the central server complex 50. There are many instances when patients interact with a healthcare provider. Examples would be individuals receiving in-patient hospital care, individuals receiving out-patient care at a hospital or clinic, and individuals resident at a nursing home, just to name a few. For example, the arrow between patients 60 and inventory 34 can represent prescriptions filled or refilled by a pharmacy. Patients can also interact directly with the central server complex 50 over the Internet or otherwise to retrieve or transmit information as described further below in the discussion of the implementation of the system depicted in FIG. 1, and can also interact with other patients.

An important aspect of the environment 10 is the ability to interact with the devices for self-testing and -treatment of medical conditions described in U.S. Pat. Nos. 8,206,340 and 9,357,961, the entire disclosures of both of which are incorporated herein by reference. One capability of those devices is to communicate with and summon emergency aid if the device detects that the user is in danger from his or her condition. As already suggested, such emergency notification can go to a participant-subscriber healthcare provider 32, who can be a hospital emergency service, a publicly administered 911 EMT service, or a private emergency responder such as Alert One® medical alert service. In addition, the same devices can record myriad information about a patient's condition, including results of the tests performed by the device, the treatment prescribed thereby, treatments actually administered using the device, warnings and other communications from the device to the patient and vice versa, just to name a few. (A more complete listing of these devices' data gathering and transmission capabilities can be found in the referenced disclosures.) All of this information can be stored by the central server complex 50 and made available to other subscribers.

A final component of the environment 10 of the present embodiment is represented by the box 70, labeled here as representing regulatory agencies and insurers. The present day healthcare landscape depends heavily on interaction and information exchange with such institutions. It will be immediately apparent that all of the interactions between the other participants (healthcare providers, manufacturers, and patients) can be structured to generate information specifically required for insurance purposes. For example, the system can provide to the central servers 50 information from a healthcare provider so that insurers (including public insurers such as Medicare and Medicaid) can access the information to process payments to the provider for care provided to a particular patient. Payments can be sent directly to the healthcare provider or to the patient automatically.

An important aspect of the invention resides in its ability to collect information and enable compliance with statutory requirements and interaction with regulatory agencies, also represented at box 70. This has particular utility in assisting participants in the environment 10 to comply with record-keeping and reporting requirements of the U.S. Food and Drug Administration (FDA) regulations such as those in Part 203 ("Prescription Drug Marketing") and Part 205 ("Guidelines for State Licensing of Wholesale Prescription Drug Distributors") of Title 21 of the Code of Federal Regulations ("C.F.R"), which implement the Prescription Drug Marketing Act of 1988, Pub. L. No. 100-293, 102 Stat. 95 (as amended by the Prescription Drug Amendments of 1992, Pub. L. No. 102-353, 106 Stat. 941). In that regard, the present invention is particularly applicable to the provisions of 21 C.F.R. Part 230, Subpart D, applicable to drug samples, defined therein as "a unit of a prescription drug that is not intended to be sold and is intended to promote the sale of the drug," 21 C.F.R. § 203.3(i). The manner in which the present embodiment implements some of those aspects of the present invention is discussed in more detail below in the description of exemplary implementations of the system represented by the environment 10. These statutes and regulations are incorporated herein in full by reference.

The healthcare environment created by the interconnected system just described has numerous advantages over prior art systems seeking just to bring more efficiency to healthcare provider operations, such as inventory and billing control systems. The present system incorporates aspects of some prior art systems, but does so using an integrated approach that includes patients, manufacturers of healthcare products, healthcare providers, and regulatory agencies and insurers. As will be appreciated as the below description of the implementation of the depicted environment proceeds, particularly as it applies to samples, manufacturers, healthcare providers (including pharmacists), and patients have the ability to track, audit, and/or replenish samples, as the case may be, from the time a sample leaves a manufacturing facility until the time it reaches a specific patient. For example, the system provides several checkpoints with accurate identities associated with each instance a sample is handled to minimize unlawful tampering or illegal sales of samples. Authenticity barcoding and/or scanning of samples can also prevent the sale or distribution of counterfeit products to consumers. This in turn will provide improved patient outcomes, support the formulation of public health policies, and make interactions between various segments of the healthcare industry more efficient. It also provides a private enterprise approach in which an administrator controls a central server system that controls and compiles information gathered in the normal operation of the system in the service of patients' needs, and makes it available to healthcare and manufacturer subscribers to the system, as well as to public and quasi-public health agencies, such as the Centers for Disease Control and Prevention. The implementation of these functionalities is discussed in the next section.

Using the Interconnected Healthcare Environment

The healthcare environment 10 embodiment of the present invention described in connection with FIG. 1 is capable of enhancing patient care in numerous ways not contemplated by the prior art. As already mentioned, one of these is the ability to monitor and control the widespread and sometimes abused practice of the provision of samples by medical product suppliers and manufacturers. The following examples of situations involving the delivery of health care to a patient will illustrate some of the ways an integrated environment with the architecture and capabilities described above can enable participants to gain a better measure of control over this widespread practice, and thus ultimately enhance patient outcomes.

Patient Care and Maintenance of Medical Records

Because the environment 10 is maintained for providing health care to a patient, the present description begins with an example of how a patient initiates participation with the environment. It will be understood that this is an example, and as this description proceeds, other ways a patient becomes a participant will become apparent. In any case, such participation might begin with a visit to a primary care physician. In a typical scenario, the patient will telephone the primary care physician to make an appointment, and the primary care physician (or his or her staff) will direct the patient to a web-based portal from which the patient can download and complete forms with the patient's medical history, insurance information, and other salient facts concerning the patient that the physician will need to be able to provide medical advice and treatment. As is conventional, the patient can either bring the completed forms to his or her initial appointment, or upload them directly to the physician's web site. This contact is one of the ways patients interact directly with healthcare providers, as represented by the arrow in FIG. 1 directly connecting patients 60 and healthcare providers 32.

The patient's participation in the environment 10 is initiated when the forms returned to the physician are stored electronically. For example, patient records can be stored locally by the physician on a database maintained by the physician (or his or her practice) via a local server or a local area network (LAN) or wide area network (WAN) interconnecting multiple facilities maintained by the practice. In addition, or instead, the same records are uploaded to the cloud-based server system 50 of the environment 10. The availability of patient records stored by the central server complex 50 is suitably limited in accordance with privacy laws, and access to particular information contained in a patient's records can be gained by other participants in the environment 10 only consistent with such laws and the conditions of their participation. In this way, the medical records of multiple patients become a part of the environment's central database maintained by the server complex 50. The salient point at this stage of the description is that an individual and his or her identification data are stored in a location that is accessible, in accordance with appropriate restrictions, to other participants in the environment, as well as to the patient. This data might also be stored as the result of a visit by a patient to a hospital emergency room or a walk-in clinic, for example, or by upload of the information by any other participant in the environment 10 who has occasion to collect such information from members of the public.

Once the patient is registered in the database maintained by the environment, each time he or she visits a healthcare provider 32 participating in the environment 10, the patient's universal medical record maintained at the central server 50 is updated. For example, this could take the form of an X-ray or other diagnostic examination and the radiologist's report based thereon, a diagnosis by a physician, the results of a visit to a dentist or oral surgeon, the issuance of a prescription for medication, or any other information related to the patient's medical condition. The information provided to the cloud-based server system will preferably include insurance information sufficient to process claims according to the patient's insurance coverage (see above) and information regarding the patient's account with the healthcare provider. Some of the purposes of recording these and other categories of information in a central location will be discussed further below. Direct communication between healthcare providers and the central server system 50 is represented by the arrows connecting the boxes 32 and 34 and the box 50 in FIG. 1.

Figure 2:
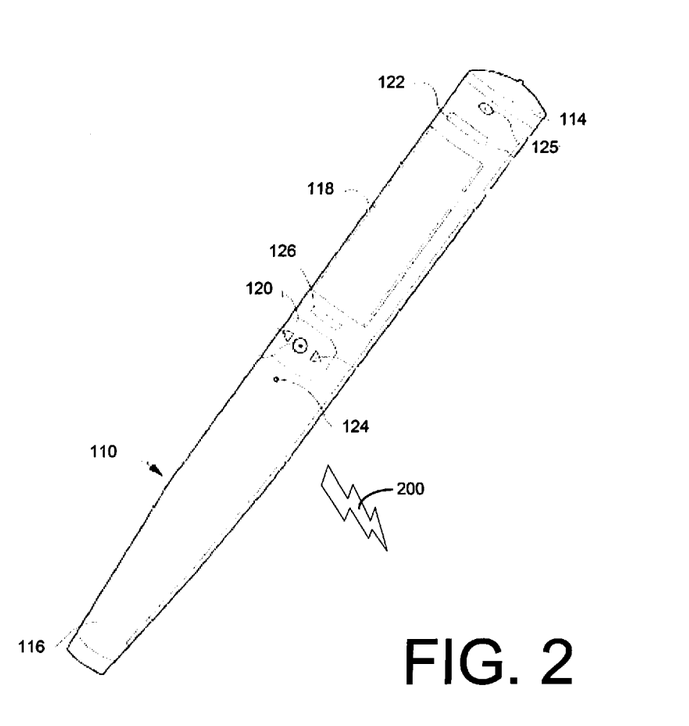
FIG. 2 depicts a portable device used for monitoring and controlling a chronic medical condition that can be incorporated into the healthcare environment shown in FIG. 1 thorough wireless communication therewith.

Another mechanism for providing information to a patient's medical record maintained on the cloud-based served system 50 is via a device as described in the present inventor's U.S. Pat. Nos. 8,206,340 and 9,357,961, the disclosures of which are incorporated herein by reference. FIG. 2 depicts a device 110 with capabilities as described in those disclosures. In one particularly advantageous embodiment, the device 110 is an integrated diabetes management pen with which a blood sample can be taken using a mechanism at a first end 114 and an insulin injection can be administered using a hypodermic needle and dosing mechanism at the other end 116. The pen 110 includes various user interface elements such as an LCD display 118 for displaying user prompts and other information, a touch device 120 for inputting instructions and other information, a speaker 122 for audible prompts, a microphone 124 with which instructions or other prompts can be input, and a video camera 125. The operation of these and other components of this type of pen-like medical device can be found in the '340 and '961 patents. As discussed in detail therein, these devices further include onboard computing capabilities that can calculate a proper insulin dosage for a particular user based on locally stored treatment protocols uploaded to the pen by a patient's healthcare provider. They can also record and store in an onboard memory information such as the treatment history of a patient (for example, times when blood samples were taken, insulin dosages calculated based thereon, actual insulin dosages administered, etc.). The devices can also place calls to emergency services (such as 911 or similar private services), and deal with numerous other circumstances encountered by the patient or user of the device.

As noted in both of the incorporated disclosures, the devices can in preferred forms include circuitry for communicating with central repositories of information relating to a patient's history of use of the device. Accordingly, such a device is particularly adapted for use with the healthcare environment 10 depicted in FIG. 1, in that it can establish communication with the server complex 50 via the schematically depicted wireless connection 200 over a WiFi connection. (Of course, the communication could also be via a hard-wired connection through a USB port 126 or other mechanism.) In this fashion, the patient's medical record stored on the server will include real-time (or near real-time) information on chronic conditions and how patients are managing them. As U.S. Pat. No. 9,357,961 in particular makes clear, the use of this type of device is not limited to diabetes treatment and management, thus enhancing the utility of the entire system in accordance with the present disclosure. Further, in accordance with an important aspect of the present invention, individual devices will be registered to individual users/patients, and information matching users to devices will be maintained as part of each user's universal electronic medical record in the database at the server complex 50.

Of particular applicability to the present healthcare environment are the portions of the '961 patent discussing the interaction and communication with healthcare "ecosystems" external to the device 110. For example, the environment 10 can include one or more, or all, of the components of ecosystems described in that application, as incorporated herein by reference. Another important feature of the device 110 as described in the '845 application in terms of certain aspects of the present invention is the device's capability of monitoring usage of various components of the device and ordering replacements (or for prompting the user that replacements are necessary) of medications and other components that the device uses. For example, the device 110 is preferably constructed so that operative parts are modular in form and can be removed and replaced in a unitary fashion. In that regard, depending on the condition it is designed to treat, the device can monitor usage of items such as (a) medications contained in a removable administration module, such as insulin, oral medications, inhalers, nasal sprays, nebulizers or other mist-related medication devices, drops and other types of inner ear medications, dermal or intradermal treatments, ointments, vaccines, elixirs, and powders, whether administered by the unit or are used in connection with the condition monitored using the unit, (b) consumables contained in a sampling module, such as lancets, testing strips, assays, dyes, and reagents, that are used in connection with the sampling and testing function of the device 110 and that are depleted as the device is used over time, and (c) hardware components such as computer memory, application chip sets, telecommunication devices, and the like that can fail and require replacement.

In the present environment, these supplies will typically be provided from an inventory 34 of a healthcare provider (see FIG. 1). Accordingly, in any particular instance the item might be a sample provided by a product manufacturer. The item will thus be coded in a suitable manner with information, such as by a bar code and/or an RFID tag or the like, as already discussed. Likewise, the device 110 will include a reader/detection apparatus under the control of device software that decodes the identification information. The device software is preferably programmed to verify that the item has been loaded into the particular device 110 registered to the intended user. Further, the device will communicate with the environment 10 to upload the information read from the item installed in the device to be included in the patient's universal medical record. The same information will be stored in a form that enables retrieval and compilation of information on each item, particularly in the case of samples, such as the item's origin (that is, information identifying the manufacturer), its batch number, type of drug, the formulation, the recommended dose, the item's expiration date, authenticity verification, and a promotional QR code optically machine-readable matrix barcode label that can be attached to the item.

Suppliers of Healthcare Products

Aspects of the environment 10 will now be described from the perspective of healthcare product manufacturers and suppliers, represented generally by the box 20 in FIG. 1. As noted above, the present embodiment uses the term "products," as represented by the box 24, and the term "manufacturers," represented by the box 22 in the broadest sense. For example, the products 24 could include drugs and medications, medical appliances, practice-management software and hardware, training and instruction manuals, and any other product or service offered to the medical profession. Specifically, the term product includes samples, as defined herein.

In a typical implementation, some or all of such items could be included in the inventory of 34 of a healthcare provider 32, under the control of the virtual closet 40. As noted already, the term "virtual closet" does not necessarily refer to particular physical locations, but rather is meant to denote a manner of controlling the items in inventory 34. Likewise, the term "inventory" does not necessarily invoke a single physical location where medical supplies are kept. For example, a hospital or clinic healthcare provider 30 might have one or more pharmacies or other supply repositories that stock items for use by healthcare personnel such as nurses and physicians in the course of treating hospital patients. In addition, the hospital or clinic could have a pharmacy at which patients or members of the general public can fill prescriptions. It will also be appreciated that a healthcare provider 30 can be a standalone pharmacy.

Figure 3:
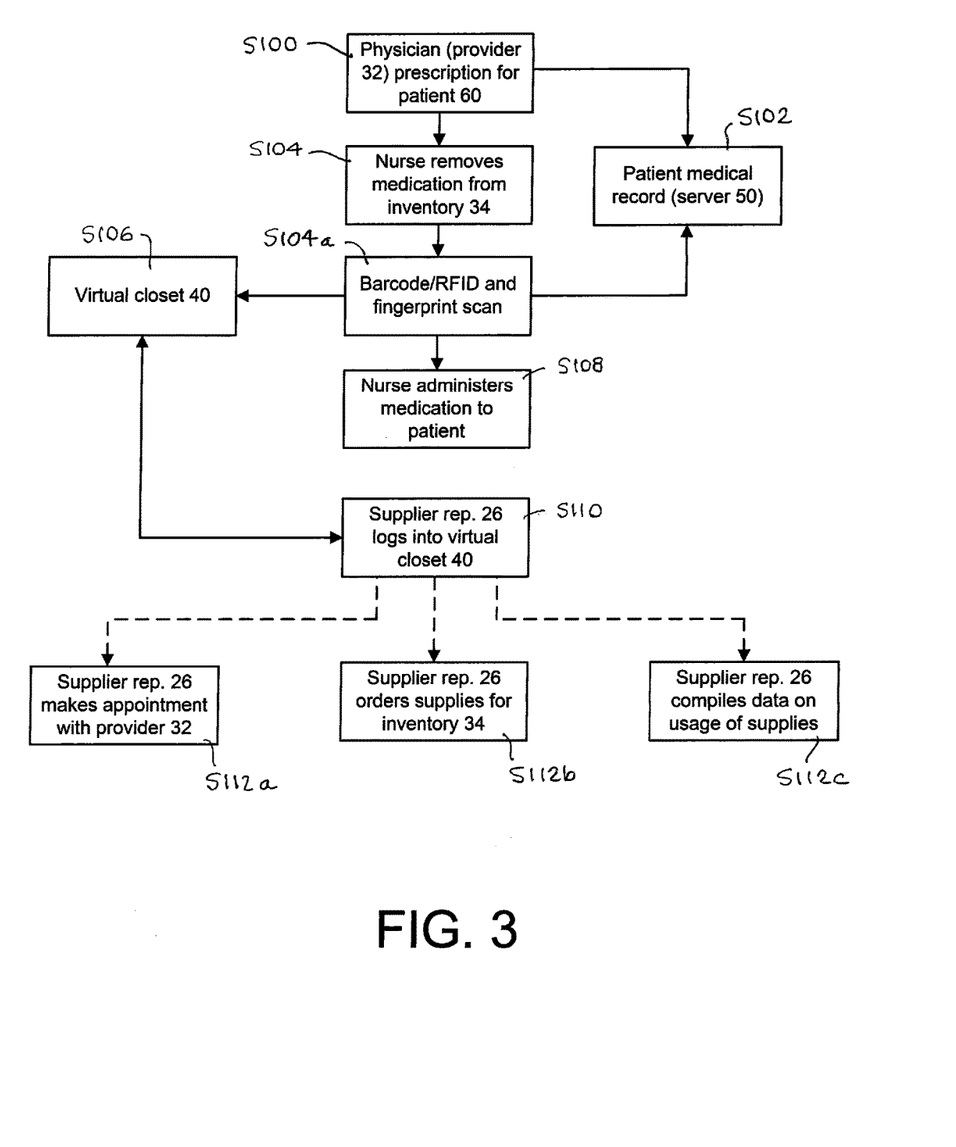
FIG. 3 is a flowchart illustrating an exemplary method by which a healthcare provider, a patient, and a pharmaceutical manufacturer can interact with the environment shown in FIG. 1.

FIG. 3 is an example of one way a supplier/manufacturer of healthcare products and/or medical supplies can interact with other participants interconnected via the environment 10. This example is described in connection with a pharmaceutical company, but those skilled in the art will appreciate that the principles illustrated are applicable to a supplier and/or manufacturer of any medical product. The process depicted in FIG. 3 begins at step S100 when a physician at a participating healthcare provider 32 prescribes a particular medication to a patient 60. In a particularly advantageous implementation of the present embodiment, the physician issues the prescription electronically via a hand-held computing device such as a laptop computer, a touch-screen activated computer (for example, an iPad® tablet computer made by Apple, Inc., or equivalent), or other forms of portable computing devices such as an iPhone® smartphone made by Apple, Inc., or their equivalent. This enables the physician to have the computing device always conveniently at hand when treating patients. One of the significant advantages of "writing" prescriptions electronically is that the prescription can be forwarded electronically to other components of the environment 10. For example, in FIG. 3, the prescription is forwarded to a local server (not shown) of the healthcare provider 32, and can then be made accessible at nursing stations, as described just below.

A portable computing device used for this implementation would have had loaded thereon software that enables the physician to suitably identify the patient, preferably by a unique code, and select from medications and dosages appropriate to that patient's condition. The device would also have the capability of permitting the physician to include notes or other instructions unique to that patient. In a particularly advantageous implementation, the physician could include observations, diagnoses, prognoses, and any other information that he or she wanted to be included in the patient's chart as part of his or her medical records stored on the server database, as discussed above. In that connection, the process in FIG. 3 includes step S102 whereby the prescription information (and other physician-provided information) is transmitted to the patient's medical records in the database therefor maintained in the cloud-based server 50.

The ability to write prescriptions electronically enables the environment 10 to include E-pharmacies that enable patients to obtain prescribed medications pursuant to prescriptions forwarded electronically from a physician healthcare provider via the cloud-based server complex to a pharmacy healthcare provider. The E-pharmacy can post on Internet web portals available to individual patients information about their prescriptions, such as when and where they will be available for pick up. The patient can also access the web portals by portable computing devices as discussed above. When the patient picks up the prescription, the pharmacy notifies the central server 50, which in turn automatically sends a notice to that effect to the physician. The system can also be programmed to provide a notice to the prescribing physician if the patient does not pick up the prescription within a predetermined time (such as three or four days). Patients or practitioners can also use the portal to facetime or video chat with an E-pharmacist should they prefer a live digital discussion regarding their prescription or pharmacy services, such as making inquiries regarding medications and treatment regimens. Another alternative to direct computer-to-computer E-prescribing that can be used with the present embodiment enables a handwritten prescription to be used by scanning it at the physician's office and then uploading it to the server complex 50. In a hospital setting, scanners can be provided at various central locations (such as one or more nursing stations on each floor of the hospital) to enable handwritten prescriptions to be scanned and entered into the system as discussed above.

Returning now to FIG. 3, when the prescription appears on a monitor or other device at a nursing station, a nurse removes the prescribed medication from inventory 34 at the healthcare provider 32, at step S104 in FIG. 3. The system can be programmed to include an audible and/or visual prompt at the appropriate nursing station(s) indicating that medication has been prescribed for a patient. If the medication is to be administered repeatedly according to a schedule, the system can be programmed to provide audible and/or visual prompts at appropriate times. The system can be programmed to require the nurse to acknowledge a prompt by pressing a key or otherwise responding to the prompt.

When the prescribed medication is removed from inventory 34, its identity is automatically sensed by a barcode or RFID scanner at step S104a in accordance with known technology, examples of which are disclosed in U.S. Pat. No. 6,996,538 and Pub. No. 2012/0173287, both of which as noted above are incorporated herein by reference. In addition, as indicated in step S104a, the person removing the item (in this case the nurse) will have his or her identity recorded via a scan of biometric data such as a fingerprint, retina, or iris recognition scan, or the like. The information on the item removed from inventory and the person removing it is sent to the virtual closet 40 in step S106. The information is compiled and available for purposes according to the invention described in further detail below. At step S108 the medication that was withdrawn from inventory 34 is administered to the patient by a nurse or other medical practitioner. The nurse registers the administration, preferably electronically at a nurses' station or on a portable computing device such as those described above. The particulars regarding the administration entered by the nurse (such as time of administration, dosage, any patient comments or nurse's comments, etc.) are automatically forwarded to the local server of the provider 32 discussed above and thence to the server 50 where it is entered into the database containing the patient's medical records. The registration by the nurse of the medication administration also can be used to disable any further prompts that can be generated by the system to remind the nurse that a prescribed medication is to be administered to the patient. It will be appreciated that the system can include other functionalities surrounding the prescription and administration of medications or other patient care protocols ordered by medical personnel for a particular patient.

An important feature associated with all of the functionalities provided by the system is that the progress of the medication or other medical product is monitored from the time it leaves the manufacturer until it is dispensed to a patient. For example, each individual handling the medical product can be identified by biometric data such as a fingerprint, retina, or iris recognition scan. Concomitantly, the product, such as a sample drug, will typically include a barcode or some other machine-readable code (such as an RIFD tag) that can be scanned or read to collect information such as that described above (origin, batch number, type of drug, formulation, recommended dose, expiration date, authenticity verification, promotional QR code, etc.). Thus, detailed information on the route of a specific sample, from manufacturer to provider inventory 34 to patient/consumer, and on each individual handling it are captured by the present system and stored in the database at the server 50.

This type of tracking is heretofore unknown and provides numerous advantages over prior art inventory and sample tracking such as that described in Pub. No. US 2012/0173287, which lacks the ability to provide this kind of detailed tracking information for specific product samples. The present system can also scan manufacturers' barcodes and/or authenticity seals and match them against stored data known to be authentic in order to identify genuine samples/treatments versus counterfeit products. The final step in the tracking process involves patient acknowledgment of receipt of the sample, preferably via an automated method such as a fingerprint scanner or the like, discussed herein. Back-up methods can include the use of patient passwords if a particular scanner malfunctions, so that the patient can still receive his or her medication. It will be further appreciated that this tracking and scanning of products as they move from source to final destination (that is, the patient) also enables detection of counterfeit samples, as well as enabling individuals responsible for patient healthcare to confirm the provenance of all medical supplies destined for consumption by the patient. With appropriate on-board software, devices such as those depicted in FIG. 2 and described above can detect and report the delivery of counterfeit, expired, or otherwise unsuitable supplies.

By creating a checkpoint each time a sample changes hands, an auditing system can be implemented that can identify any mishandling of products and where it may have occurred. Part of the data generated by a tracking method according to this aspect of the invention is a receipt for each transaction (physical or digital) that can be made available to participants. These receipts enable after the fact audits of particular physicians' use of samples in accordance with the parameters of the Prescription Drug Marketing Act or other regulatory mechanisms, since the records created by the tracking method can be used to compile information such as the number and/or dollar amount of samples received by a physician as reported to the FDA by manufacturers against the physician's license number/name. The receipt paradigm employed in this aspect of the present invention can be used for other accounting, tax, and compliance services, as well. Physicians can also set limits on the number and/or dollar amount of samples they wish to receive from particular manufacturers. For example, a physician may set a limit of $50,000 per year on the value of gratuities (including samples) received from a manufacturer, and the system can make available to the physician in real time the dollar amount of gratuities provided to the physician being reported to relevant regulatory bodies being reported by that manufacturer's representatives. The system can further be programmed to provide automatic alerts to the physician as the reported amount approaches the limit set by the physician.

It will be understood that steps S100 to S108 in FIG. 3 represent an example of one transaction affecting the inventory 34 at a single healthcare provider 32. Although a hospital setting was used in this example, similar principles and procedures can be employed in a physicians' office, an ambulatory care facility, a clinic, and the like, when a physician prescribes a medication or procedure for a patient at step S100. In any instance in which the medication is a sample to be given to the patient at the time of a visit to a physician's office, for example, it is removed from inventory and the above described data identifying the sample is recorded pursuant to the virtual closet concept discussed above. The same applies if the prescription is later filled by the patient at a pharmacy. In addition, in one advantageous implementation of the invention, the item can be automatically sent to a patient in accordance with an "order" placed electronically from a portable device such as the device 110 when a medication or sampling module requires replacement. In that event, the device then automatically sends confirmation of the installation of the item into the device per the description above.

It will be appreciated that all of the transactions involving withdrawals from inventory at multiple healthcare providers result in the accumulation of data on the use of medical supplies by each of the healthcare providers that participate in the environment 10, and data on all of the medical supplies that they have in their respective inventories 34. This data can be used by the manufacturers and suppliers of medical suppliers in a variety of ways, some of which are represented in FIG. 3. In step S112 a representative 26 of a manufacturer logs into the virtual closet to obtain data therefrom that can be used for a variety of purposes. For example, in step 112a the representative 26 checks to see if a particular healthcare provider treats a large number of patients with a particular condition for which the manufacturer he represents has a new medication about to become available. In that instance, the representative can send a message through the server 50 (for example, an e-mail) to a contact at the provider to set up an appointment to introduce the new medication and provide samples. In step 112b the representative can determine if the inventory of particular supplies for which a provider 32 has a standing order is low and can order replacements for restocking the inventory 34 of that supplier.

In the same fashion that withdrawals of supplies are monitored automatically by using RFID tags or barcodes on products and biometric data scans, replenishment of supplies and the person performing the replenishment are recorded (as in step S104a) so that the status of the virtual closet 40 is updated and a receipt can be created for the transaction. In step 112c the representative 26 can look for and fill orders for supplies placed by healthcare providers. It will be understood that steps 112a to 112c are merely examples of the ways that data accumulated in the virtual closet 40 can be used. Communications between healthcare providers and supplier representatives can be managed in accordance with the disclosure in Pub. No. US 2012/0173287.

Control of Interactions with Manufacturers' Representatives and Samples

In accordance with current practice, there are many ways that manufacturers' representatives interact with healthcare providers, but heretofore there has not been any comprehensive manner of managing the myriad aspects of those interactions with air eye toward regulatory compliance, maintenance of healthcare provider records, and preventing mishandling of medical products, including samples, just to name a few of the considerations involved in such interactions. It is also necessary to incorporate into a system for managing these interactions a way of maximizing positive patient outcomes. The following describes some examples of typical interactions between manufacturers' representatives and healthcare providers effectively managed in accordance with the present invention.

In one such example, an individual at a manufacturer ships a sample (which may include more than one item of the same drug) to a distributor. At that time the individual scans his or her fingerprint and an authenticated bar code/seal on the sample, and this information is recorded and stored. The system software also this sample a unique identity for tracking purposes. This creates an electronic manufacturer's shipping record that associates the sample (via the unique identity code) and the individual who shipped it. The person at an intermediate party such as the distributor receiving the sample likewise scans her fingerprint and the product bar code to create an electronic distributor receipt that associates the sample with that person. The same or a different individual at the distributor ships the sample to a sales representative of the manufacturer, and the individual at the distributor who actually ships the sample and the sales representative who receives it both record by fingerprint scan or other identification means such as a retina scan or the like (see above) and by scanning the sample bar code seal. This creates an electronic distributor shipping record and an electronic sales representative receipt, each of which associates the sample with the individual handling the sample. Accordingly, a record of the route of the sample and of the individuals at intermediate parties handling same since leaving the manufacturer is created and stored in the central server 50 of the present system. The sales representative then visits a healthcare provider with the intent of providing the sample for the provider's use with its patients.

Using a registered and licensed physician as an example of a healthcare provider in this instance, the representative delivers the samples. In current practice, the physician or a person authorized by him or her must sign for the samples to acknowledge the receipt of same. In a system according to the present invention, this event is also captured and stored, in the form of an electronic provider receipt that associates the sample and the individual who received it on behalf of the healthcare provider, thus providing a traceable route for specific, identifiable samples from manufacturer to physician. Any mishandling is thus readily identified because all of the specifics of the particular samples delivered to the physician, such as the number received and shipped at each point in the chain, the individuals handling the samples, and the like, have been recorded and stored.

This process results in the creation of a unique record each time the sample changes hands. That is, broadly speaking, once a unique machine-readable code is assigned to a sample, one method aspect of the invention creates a record each time it is handled. Such a method thus involves assigning a machine-readable unique code to the sample and withdrawing the sample from inventory at the manufacturer. At that time, the unique code is scanned, preferably automatically as the sample is removed from a repository at the manufacturer. The unique code and a unique identity of the individual withdrawing the sample are stored as a first record relating to the sample. When the sample is thereafter shipped to an intermediate party (such as a distributor or the manufacturer's representative), the unique code is again scanned and stored with a unique identity of the individual receiving the sample at the intermediate party to create a second record relating to the sample. When the sample is finally shipped to the healthcare provider, the unique code is scanned upon arrival and stored, along with a unique identity of the individual receiving the sample at the healthcare provider, to create a third record relating to the sample.

The present invention is particularly adapted for use with a hand-held touch screen device such as an Apple iPads®. In the example just given, what typically happens when the representative delivers the samples to the physician, a person at the physician's reception desk or other office personnel is given the representative's touch screen to collect the necessary signature directly thereon. To guard against sample mishandling and fraud, an aspect of the invention includes software resident on the representative's device to authenticate the signature and thus detect unauthorized signatures.

During the same visit the representative may have a discussion with the physician and may have incurred costs associated with a meal at a restaurant or provided another gratuity such as a reprint of an article in a medical journal regarding drugs of the manufacturer for whom the representative works or a book relating to the physician's specialty. Each such resource provided to the physician that has a cost associated with it must be reported by the representative under various statutes and regulations, such as the Physician Payment Sunshine Act, section 6002 of the Patient Protection and Affordable Care Act, Pub. L. 111-148. This statute requires that health providers report their sources of funding, the purpose being to increase patient safety by increasing transparency in conflicts of interest between health care providers and any outside interest. Manufacturers of drug, medical devices, and biological and medical supplies must report certain payments, gifts, and other items of value to physicians, and that information will be available to the public. The present invention provides a convenient way for a representative to satisfy this obligation, by including software provided by the manufacturer and resident on his or her hand-held device that creates a report uploaded to the servers 50 and then made available to the appropriate governmental agencies. Thus, a manufacturer's representative can account for each item left with the health provider.

From the perspective of the physician, he or she may or may not have systems in place to track what the representatives the physician deals with are reporting under his or her license or name. Thus, the physician can easily be unaware of the amount a manufacturer "spends" and reports vis-à-vis that physician until they are identified in the public reports required by law. An aspect of the present invention enables physicians to track the spend amounts and also to identify false spend reporting by a manufacturer. In accordance with the above discussion directed to the provision of drug samples, the present system can generate receipts associated with each reportable interaction between a physician and a representative will involve representatives scanning their fingerprints, for example, and the product bar code of the item given to the physician (the sample, voucher, coupon, reprint, gift, etc.), or to associate a meal expense with the interaction. This provides both parties a record of the interaction and the dollar amount associated with it. In addition, if the system is implemented in a way that requires the physician to verify by signature (for example, on the representative's hand-held touch screen device) receipt of any item of value, including gratuities such as meals and books, it provides additional protection against the fraudulent use of the physician's license number and helps avoid any false reporting by a manufacturer.

The physician or other provider will typically have one or more employees manage the sample inventory. In a common installation, samples are placed in a dedicated sample closet or designated physical space for storage (part of the inventory 34 in FIG. 1). This implementation can use a modified monitoring system such as that used for library security such as the RFIQ™ security system marketed by D-Tech International LLC USA, 121 W. Morning Glory Road, Wildwood Crest, N.J., 08260. A reader is mounted on the closet door or filing drawer to sense each time a sample is placed in or removed from the closet by an employee of the physician or a manufacturer representative. Everyone removing samples is also scanned for identification. (See step S104a in FIG. 3.) Thus, a sample electronically logged into inventory will be electronically logged out as well, with the individual performing the stacking or withdrawal of the sample being identified. As described above, the sample will be also associated with a particular patient, who can be identified by a fingerprint scan or the like on a hand-held device when the sample is delivered to the patient. This direct connection between sample and patient will be advantageous to manufacturers, providers and regulatory agencies. As one example, in the event of a recall of a sample drug, the identity of every patient to who it was dispensed will be readily available to all parties concerned, including relevant regulatory agencies and public health organizations.

Summary and Additional Features of the Present Invention

As will be appreciated, a healthcare environment implemented in accordance with the above description provides a universal portal to access all healthcare manufacturing sites, product information, vouchers and additional resources. It enables validation of the authenticity of manufacturer websites to eliminate "spoof" websites that target health providers and consumers, and solicits health and financial information by acting as a secure, password-protected portal for accessing manufacturer resources, samples and information via one convenient platform. No other integrated healthcare system is known to provide a manner of accessing resources, such as manufacturers' sample vouchers that patients can download and print, and other resources made available to consumers by manufacturing companies. For example, if a patient wants information on Spiriva®, a medication used for chronic obstructive pulmonary disease (COPD), the patient would go to www.spiriva.com to print coupons or free sample trial vouchers (made available with a prescription). The coupon vouchers are supplied by manufacturers and serve as discount cards, which can reduce insurance copays to as low as $10/month. The present invention provides a universal platform that has only certified links to manufacturers' websites to help patients avoid accessing fraudulent sites. The patient portal provided by the system can organize all manufacturer samples, product information, resources, and can provide a scanning application that patients can download to scan samples and medication bar codes to confirm sample authenticity.

The environment of the present invention also provides a platform that can facilitate electronic interaction between healthcare providers and manufacturers, consumers and manufacturers, consumers and healthcare providers, and healthcare providers and patients. For example, "electronic" representatives available through chat rooms or e-mail established as part of the environment 10 can answer patient questions regarding product samples and provide customer service, technical support, clinical support, event coordination (such as scheduling visits from manufacturers' representatives, or patient wellness seminars, as two examples), managed care, indigent patient programs, and a way to report adverse events form a drug or other medical product.

The present invention provides a universal platform which allows manufacturers to provide available resources including sample vouchers, coupons, educational materials, calendar events, clinical trial information, advance news on upcoming products or product improvements, news updates, regulatory approval information, directories with contact information for participants in the environment, and electronic representative interfaces via a single site. Thus, one aspect of the invention provides a clearinghouse which organizes all of a manufacturer's resources under one site making it easier for manufacturers to make real-time updates of relevant information, provides physicians with a single location where they can retrieve tools and resources they need for patient care, and gives patients access to accurate, up-to-date manufacturer information needed to manage their care.

Those skilled in the art will readily recognize that only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A method of creating an electronic medical record that enables confirmation of the integrity of a supply chain of a particular medical product for treating a particular medical condition of a particular patient, the particular medical product being uniquely identified by a product code applied by a manufacturer, from the time a medical product is shipped from the manufacturer until a medical product reaches the particular patient to be loaded into a portable medical device capable of using the particular product to treat the particular medical condition of the patient, wherein the device stores a unique electronic patient code associating the device with the particular patient and includes (i) reading/detection apparatus for creating an electronic compliance record by reading a product code applied to a medical product loaded into the device, and (ii) communication circuitry for sending the patient code and the compliance record from the device to a remote storage location, the method comprising:

storing at the storage location the product code applied to the medical product by the manufacturer;

storing a manufacturer's shipping record at the storage location when a medical product intended for a particular medical device leaves the manufacturer's custody, wherein the manufacturer's shipping record is created by reading a product code applied to the medical product and associating a resulting electronic shipped-product code with a unique identity in electronic form that is indicative of an individual shipping the product from the manufacturer;

storing an intermediate party receiving record at the storage location when a medical product is received by an intermediate party, wherein the intermediate party receiving record is created by reading a product code applied to the received product and associating a resulting electronic received-product code with a unique identity in electronic form that is indicative of an individual receiving the product at the intermediate party;

storing an intermediate party forwarding record at the storage location when a medical product is forwarded from the intermediate party intended for delivery to the patient, wherein the intermediate party forwarding record is created by reading a product code applied to the forwarded product and associating a resulting electronic forwarded-product code with a unique identity in electronic form that is indicative of an individual forwarding the product from the intermediate party;

associating the patient code at the storage location with a unique electronic device code identifying a particular medical device associated with the particular patient;

using the compliance record created by the reading/detection apparatus and received at the storage location via the communication circuitry to signify that a medical product was loaded into the device;

when the compliance record matches the product code applied by the manufacturer, creating a medical record associated with the particular patient confirming that the particular medical product was loaded into the particular device;

storing the medical record at the storage location for access by authorized individuals; and when the compliance record does not match the product code applied by the manufacturer, identifying from the respective unique identities at least one of the individual shipping the product from the manufacturer, the individual receiving the product at the intermediate party, and the individual forwarding the product from the intermediate party associated with a respective shipped-product code, received-product code, and forwarded-product code that does not match the product code applied by the manufacturer.

2. A method as in claim 1, wherein one intermediate party receiving the product sends it to another intermediate party, the method further comprising storing at the storage location a separate intermediate party receiving record each time a product is received by each intermediate party and a separate intermediate party forwarding record each time a product is forwarded from each intermediate party.

3. A method as in claim 2, wherein the intermediate parties include at least one distributor of medical products who receives products from the product manufacturer and a sales representative of the product manufacturer who delivers products from the product manufacturer to a healthcare provider.

4. A method as in claim 1, wherein access to the medical record and the device code is controlled by the particular patient.

5. A method as in claim 1, wherein the unique identity assigned to each individual is created by a biometric scan of the individual and the product code applied to the product comprises at least one of a bar code or an RFID tag attached to the product.

6. A method as in claim 1, further comprising:

storing a healthcare provider receiving record at the storage location when a medical product is received by a healthcare provider from an intermediate party, wherein the healthcare provider receiving record is created by reading a product code applied to the received product and associating a resulting electronic provider-receipt code with a unique identity in electronic from that is indicative of an individual receiving the product at the healthcare provider; and when the compliance record does not match the product code applied by the manufacturer, identifying from the respective unique identities at least one of the individual shipping the product from the manufacturer, the individual receiving the product at the intermediate party, the individual forwarding the product from the intermediate party, and the individual receiving the product at the healthcare provider associated with a respective shipped-product code, received-product code, forwarded-product code, and provider-receipt code that does not match the product code applied by the manufacturer.

7. A method as in claim 6, wherein the medical product is maintained in a repository at the healthcare provider and the product code applied to the product is scanned automatically when the product is removed from the repository.

8. A method as in claim 7, wherein the product comprises one of a consumable item for the device, a module containing a medication for administration using the device, and a replacement hardware item for the device.

9. A method as in claim 6, wherein the product comprises a sample provided by the manufacturer for free or at a cost below the normal price charged to users for the product and the product code of the sample loaded into the device includes the patient code indicative of a particular patient for whom the sample is intended.

10. A method as in claim 9, wherein the sample comprises one of a consumable item for the device, a module containing a medication for administration using the device, and a replacement hardware item for the device.

11. A method as in claim 6, wherein the unique identity assigned to each individual is created by a biometric scan of the individual and the product code applied to the product comprises at least one of a bar code or an RFID tag attached to the product.

12. A method as in claim 1, wherein the product comprises one of a consumable item for the device, a module containing a medication for administration using the device, and a replacement hardware item for the device.

13. A method as in claim 1, wherein the communication circuitry comprises at least one of WiFi circuitry and cellular telephone circuitry.

14. A method as in claim 1, wherein the storage location receives the compliance record from the device at substantially the same time that it is created.

15. A method as in claim 1, wherein the storage location comprises plural cloud-based servers.

* * * * *